United States Patent [19]

Shank

[11] 4,062,890
[45] Dec. 13, 1977

[54] PROCESS FOR MANUFACTURE OF ISOBUTYLIDENE DIUREA

[75] Inventor: Joseph L. Shank, Matteson, Ill.

[73] Assignee: Swift Agricultural Chemicals Corporation, Chicago, Ill.

[21] Appl. No.: 580,218

[22] Filed: May 23, 1975

[51] Int. Cl.² ............... C07C 127/15; C05C 9/00
[52] U.S. Cl. .................... 260/553 R; 71/28
[58] Field of Search .............. 71/28; 260/553 R

[56] References Cited

U.S. PATENT DOCUMENTS

| | | | |
|---|---|---|---|
| 2,810,710 | 10/1957 | Long | 71/28 X |
| 3,192,030 | 6/1965 | Mills et al. | 71/28 X |
| 3,219,432 | 11/1965 | Schäfer et al. | 71/28 |
| 3,227,543 | 1/1966 | O'Donnell | 71/28 |
| 3,231,363 | 1/1966 | Renner | 71/28 X |
| 3,232,739 | 2/1966 | Belak | 71/28 |
| 3,322,528 | 5/1967 | Hamamoto et al. | 260/553 R X |
| 3,326,665 | 6/1967 | Schäfer et al. | 71/28 |
| 3,365,468 | 1/1968 | Feichtinger | 260/553 R X |
| 3,649,598 | 3/1972 | Namioka et al. | 71/28 X |
| 3,677,736 | 7/1972 | Formaini | 71/28 |

OTHER PUBLICATIONS

Schäfer et al., "Mixed Nitrogen Fertilizers," CA 56:P14658a. (1962).
Christianson, "Water-reducible, fire-retardant coating compositions", CA 48:14247b, (1954).

*Primary Examiner*—Daniel E. Wyman
*Assistant Examiner*—Thomas A. Waltz
*Attorney, Agent, or Firm*—Edward T. McCabe; Charles E. Bouton; Robert E. Blankenbaker

[57] ABSTRACT

A process for manufacturing isobutylidene diurea (IBDU) comprising reacting urea with isobutyraldehyde in an aqueous medium and in the presence of a protein-derived emulsifier and an inorganic ammonium salt.

9 Claims, No Drawings

PROCESS FOR MANUFACTURE OF ISOBUTYLIDENE DIUREA

This invention relates to the manufacture of compositions having utility as slow nitrogen release fertilizers, and in particular, relates to the manufacture of isobutylidene diurea.

Prior art techniques of manufacturing IBDU generally involve reaction of urea with isobutyraldehyde in an aqueous, acidic solution with vigorous mixing. For example, see U.S. Pat. Nos. 3,322,528; 3,326,665; and 3,441,539. Also, see Great Britain Pat. Nos. 949,408; 1,099,643; and 1,212,605. The primary drawback of these prior art techniques of manufacturing IBDU is the relative lack of control over the condensation reaction. That is, the reaction rate and total time of reaction is most difficult to control. Often, such condensation reactions proceed at a rather slow and unpredictable pace, frequently requiring a 10 to 30 minute reaction time. There is, therefore, a continuing need in the art for improved techniques of manufacturing IBDU.

It is therefore a primary objective of the present invention to provide an improved process for manufacturing isobutylidene diurea.

It is also an objective of the present invention to provide an improved process for rapidly reacting urea with isobutyraldehyde in an alkaline pH aqueous reaction medium.

It is a further objective of the present invention to provide an improved process for reacting urea with isobutyraldehyde in the presence of a bio-degradable emulsifier.

It is an additional objective of the present invention to provide an improved process for reacting urea with isobutyraldehyde in the presence of an inorganic ammonium salt accelerator.

Briefly, the objectives of this invention are carried out by reacting an aqueous urea solution with isobutyraldehyde at an alkaline pH. The normally immiscible aqueous and organic phases are emulsified by the presence of a protein-derived, bio-degradable emulsifier. Also, the reaction is accelerated by the presence of an inorganic ammonium salt.

Initially, the solid urea should be dissolved in water to form an aqueous reaction phase. Preferably, the urea solution should contain urea at a concentration of from about 40% to 80% by weight. Generally, the higher the concentration of urea in solution (and consequently, the less the amount of water), the faster the condensation reaction will proceed. Addition of isobutyraldehyde to the aqueous urea solution, along with slight heating of the reaction mixture, results in a condensation reaction between the urea and the isobutyraldehyde in which two moles of urea react with one mole of isobutyraldehyde to form IBDU and water. Preferably, the urea and isobutyraldehyde are present in the reaction mixture in approximately stoichiometric amounts of about 2 moles urea per mole of isobutyraldehyde. However, the reaction will proceed in the presence of molar excesses of either reactant.

I have discovered that a more rapid and controlled reaction can be achieved by reacting the aqueous urea solution with isobutyraldehyde in the presence of a protein-derived emulsifier. I prefer to employ a collagen-derived emulsifier in the amount of about 1 to 10% by weight of the reaction mixture. Collagen is native animal protein which is insoluble in water. However, collagen may be hydrolyzed by heating in acid solution, such that the collagen is broken down to lower molecular weight components such as gelatin and glue. Glues derived from collagen in this manner exhibit excellent emulsifying properties in the manufacture of IBDU. Preferably, the collagen-derived emulsifier should be in a liquid form when added to the reaction mixture. Thus, an aqueous system of the collagen-derived emulsifier can be employed. Such a system can be prepared by suspending animal glue in water up to a concentration of about 50% by weight. Also, a minor amount of urea (up to about 50% by weight of the glue) can be beneficially incorporated into such an emulsification system to serve as a liquefying agent for the glue. Thus, a typical liquefied emulsifier system in accordance with this invention might comprise a colloidal suspension containing about 40% animal glue, about 15% urea and about 45% water. An additional advantage of using a collagen-derived emulsifier system is its inherent bio-degradability. Thus, where the emulsifier is present in association with IBDU reaction products used as fertilizers, the bio-degradable emulsifier will break down in the soil, contributing nitrogen and carbon thereto.

Since the aqueous urea phase and the organic isobutyraldehyde phase are normally immiscible, prior art techniques have emphasized the importance of vigorous mixing of the two phases during reaction so as to insure contact of the reactants. I have discovered that emulsification of the reaction system with a collagen-derived emulsifier, along with vigorous agitation, results in a more rapid and uniform reaction. By emulsifying the organic and aqueous phases of the reaction mixture, more intimate contact between the reactants is obtained than can be achieved by agitation alone. This results in a more rapid and controlled reaction between the urea and isobutyraldehyde.

I have also discovered that the presence of from about 0.5% to 10% by weight of the reaction mixture of an ammonium salt accelerator promotes reaction speed and uniformity. In particular, it has been determined that inorganic ammonium salts, and preferably polyvalent inorganic ammonium salts, function to accelerate the reaction of urea with isobutyraldehyde. The two most preferred accelerating agents are ammonium sulfate and ammonium phosphate.

A preferred mode of carrying out this invention involves mixing the desired amounts of urea, collagen-derived emulsifier and inorganic ammonium salt with water, and heating this aqueous phase to a temperature in excess of about 40° C. Thereafter, addition of the desired amount of isobutyraldehyde to the aqueous reaction medium, along with vigorous agitation, results in emulsification of the system and an immediate condensation reaction between the urea and isobutyraldehyde. Since the condensation reaction is exothermic, external heating is not required once the reaction has been initiated. Rather, the heat of exotherm is allowed to increase the reaction medium temperature until the condensation reaction has been substantially completed. Usually, the exothermic condensation reaction will increase the reaction temperature to from about 65° C. to 100° C. Due to the presence of the urea and inorganic ammonium salt, and the absence of any prior art acidic catalysts, the reaction proceeds at a pH of from about 7.0 to 9.0. Within the first 2–3 minutes of reaction, the reaction mass progresses from a creamy texture to a soft solid. At this time, the reaction mass should be removed from the reaction vessel, and the exothermic condensation reaction is allowed to proceed until completed. In accordance with this invention, it has been determined that substantially complete reaction between the urea and isobutyraldehyde can be obtained within a period of from about 2 minutes up to about 15 minutes. Of course, total time of the reaction is a function of many parameters, including reactant concentration, reaction temperature and degree of agitation.

The above-described condensation reaction can be carried out batchwise as in a closed kettle with scraper blades. Preferably, the reaction is performed in a closed system continuous reactor. For example, the reaction can be carried out in a pipe reactor or a closed system screw conveyor. Completion of the condensation reaction results in a granular or chunky mass containing about 40% to 60% solids, and comprising isobutylidene diurea and water.

This product is then dried to a pre-determined moisture content. Where the isobutylidene diurea is to be used as a slow nitrogen release fertilizer, it is preferable to dry the reaction product to a moisture content of less than 10%, and most preferably to a moisture content of less than 1%. Drying is normally carried out in conventional equipment such as oven dryers or drum dryers.

The dried reaction product, which comprises lumps of isobutylidene diurea, is then fed through an appropriate grinding apparatus to yield an IBDU powder which is then fed to a compactor. Compaction is generally carried out at a pressure of from about 70 to 140 kg. per square centimeter (1,000–2,000 psig.), and preferably at about 105 kg. per cm.$^2$ (1,500 psig.). The IBDU exhibits thermoplastic properties during compaction such that the intense pressures used, and heat generated thereby, causes the product to flow together, forming a dense sheet having a surface sheen. The IBDU sheet is then fed through a conventional grinder or granulator in order to provide a pre-determined product particle size. For example, an IBDU powder can be obtained by finely grinding the sheet and classifying the ground particles to a size of approximately 30–80 mesh. Preferably, however, the IBDU sheet is granulated and classified to a mesh size of approximately 5–30 mesh granules. Although IBDU powder exhibits slow nitrogen release properties, such powders will dissolve in the soil more rapidly than larger IBDU granules. Thus, IBDU granules will often take up to six months or longer to totally dissolve when present in the soil, thus providing many months of nitrogen release to crops. It should also be noted that isobutylidene diurea prepared in accordance with this invention can be utilized as a ruminant feedstuff as described in U.S. Pat. No. 3,642,488.

EXAMPLE I

To illustrate a preferred embodiment of the present invention, the following ingredients were weighed into a beaker:

| (1) | Urea | 100 grams |
|---|---|---|
| (2) | Water | 100 grams |
| (3) | Ammonium sulfate | 5 grams |
| (4) | Aqueous solution of collagen-derived protein liquefied with urea (50% protein) | 5 grams |

The above ingredients were dissolved in water at about 50° C. with mixing. Thereafter, 60 grams of isobutyraldehyde were added with rapid mixing. The reaction emulsion progressed from a white fluid to a thick cream to a soft solid within 2 minutes, at which time the temperature had increased to about 65° C. The reaction mass was then removed from the reaction vessel, and the condensation reaction allowed to continue until completion, which required an additional 10 minutes, the reaction temperature rising to a maximum of 95° C. The resulting reaction product had a lumpy consistency, comprised about 55% solids, and was relatively dry to the touch.

EXAMPLE II

Example 2 of U.S. Pat. No. 3,322,528 to Hamamoto, et al., was carried out by adding the following ingredients to a beaker:

| (1) | Urea | 66 grams |
|---|---|---|
| (2) | Water | 66 grams |
| (3) | Isobutyraldehyde | 36 grams |

The reaction mixture was heated to 55° C. with mixing, and then removed from the hot-plate. Mixing was continued until the condensation reaction was completed as indicated by a drop in temperature from the maximum of 72° C. reached. The reaction mixture required 28 minutes to completely react, and the reaction product was pasty in consistency. This Example illustrates a typical prior art technique of manufacturing IBDU as requiring a longer reaction time, and resulting in a wetter product which requires increased drying.

EXAMPLE III

To show the importance of the inorganic ammonium salt in promoting the condensation reaction, the following reaction mixtures were prepared:

| SAMPLE A | |
|---|---|
| (1) Urea | 100 grams |
| (2) Water | 35 grams |
| (3) Collagen-derived emulsifier | 5 grams |
| (4) Ammonium phosphate | 10 grams |
| (5) Isobutyraldehyde | 70 grams |
| SAMPLE B | |
| (1) Urea | 100 grams |
| (2) Water | 35 grams |
| (3) Collagen-derived emulsifier | 5 grams |
| (4) Potassium Phosphate | 10 grams |
| (5) Isobutyraldehyde | 70 grams |

Both reaction mixtures were heated to 55° C. with stirring, then removed from external heating. Sample A reached a maximum temperature of 87° C. (indicating completion of the condensation reaction) in only 8 minutes. The reaction product was a relatively dry, granular solid. Sample B reached a maximum temperature of 67° C., but the reaction mixture remained liquid at that temperature. The system was then externally heated to 82° C. to complete the reaction. The total reaction required 32 minutes, and the reaction product was an amorphous paste.

Obviously, many modifications and variations of the invention as hereinbefore set forth may be made without departing from the spirit and scope thereof, and therefore, only such limitations should be imposed as are indicated in the appended claims.

I claim:

1. A process for manufacturing isobutylidene diurea comprising reacting an aqueous solution of urea with isobutyraldehyde at a pH of from about 7.0–9.0 and in the presence of from about 1–10% by weight of a glue or gelatin protein emulsifier derived from collagen and in the presence of from about 0.5-10% by weight of a polyvalent inorganic ammonium salt reaction accelerator.

2. The process of claim 1 wherein the aqueous urea solution has a urea concentration of from about 40% to about 80% by weight.

3. The process of claim 2 wherein the urea and isobutyraldehyde are present in approximately stoichiometric amounts.

4. The process of claim 3 wherein the emulsifier comprises a liquefied animal glue.

5. The process of claim 4 wherein the ammonium salt is selected from the group consisting of ammonium sulfate, ammonium phosphate and mixtures thereof.

6. The process of claim 5 wherein the reaction mixture is heated to in excess of about 40° C to initiate reaction.

7. The process of claim 6 wherein the aqueous reaction mixture is thoroughly agitated.

8. The process of claim 6 wherein the reaction product is dried to a moisture content of less than about 1%, and is then ground to a powder and compacted into a solid sheet.

9. The process of claim 8 wherein the isobutylidene diurea sheet is granulated and classified through screens to obtain slow nitrogen release fertilizer granules having a particle size of from about 5-30 mesh.

* * * * *